United States Patent [19]

Babin et al.

[11] Patent Number: 5,237,106
[45] Date of Patent: Aug. 17, 1993

[54] REACTIVATION OF HYDROFORMYLATION CATALYSTS

[75] Inventors: James E. Babin, Hurricane; David R. Bryant; Arnold M. Harrison, both of South Charleston; David J. Miller, Charleston, all of W. Va.

[73] Assignee: Union Carbide Chemicals & Plastics Technology Corporation, Danbury, Conn.

[21] Appl. No.: 825,083

[22] Filed: Jan. 24, 1992

[51] Int. Cl.$^5$ ........................ B01J 38/62; C07C 45/49
[52] U.S. Cl. .................................. 568/454; 502/28; 556/21
[58] Field of Search ............................ 568/454; 556/21; 502/28

[56] References Cited

U.S. PATENT DOCUMENTS

| | | | |
|---|---|---|---|
| 3,555,098 | 1/1971 | Olivier et al. | 260/604 |
| 4,292,196 | 9/1981 | Homeier et al. | 252/412 |
| 4,845,306 | 7/1989 | Puckette | 568/454 |
| 4,861,918 | 8/1989 | Miller et al. | 568/454 |
| 4,929,767 | 5/1990 | Miller et al. | 568/454 |
| 5,183,943 | 2/1993 | Bryant et al. | 568/454 |

FOREIGN PATENT DOCUMENTS

| | | |
|---|---|---|
| 216315 | 4/1987 | European Pat. Off. |
| 43-022571 | 9/1968 | Japan |
| 51-014482 | 5/1976 | Japan |
| 56-033040 | 4/1981 | Japan |
| 1219763 | 1/1971 | United Kingdom |

OTHER PUBLICATIONS

"Hydroformylation of Alkanes by Use of Rhodium Complex Catalysts" by Evans et al in the *J. Chem. Soc. A*, 1968 pp. 3133-3142.

"Reactivation of Rhodium Hydroformylation Catalysts by Treatment with Aqueous Sodium Bicarbonate" by Anonymous in *Research Disclosure*, Nov. 211, (1981), p. 393, #21103.

U.S. appln. Ser. No. 670,874 filed Mar. 18, 1991 Reactivation of Hydroformylation Catalysts.

*Primary Examiner*—Marianne M. Cintins
*Assistant Examiner*—Michael B. Hydorn
*Attorney, Agent, or Firm*—R. J. Finnegan

[57] ABSTRACT

A process for improving the catalytic activity of a partially deactivated solubilized rhodium-tertiary organophosphine complex hydroformylation catalyst by treating it with propargyl alcohol and a carboxylic acid.

15 Claims, No Drawings

REACTIVATION OF HYDROFORMYLATION CATALYSTS

This invention relates to a process for improving the activity of partially deactivated rhodium-tertiary organophosphine complex hydroformylation catalysts.

BACKGROUND OF THE INVENTION

Processes for forming aldehyde products by the hydroformylation reaction of an olefinic compound with carbon monoxide and hydrogen in the presence of a rhodium-tertiary organophosphine complex hydroformylation catalyst are well known in the art. Of particular interest are those hydroformylation reactions designed to produce aldehydes at low pressures, such as disclosed, e.g., in U.S. Pat. Nos. 3,527,809; 4,148,830; 4,247,486; and 4,731,486.

Commercial experience has shown that, even in the substantial absence of extrinsic catalyst poisons, rhodium-tertiary organophosphine complex catalysts lose activity (i.e. become partially deactivated) during the course of continued prolonged hydroformylation, and such is commonly referred to as intrinsic deactivation. While it is difficult to ascertain the precise reasons for such lose in activity, such intrinsic deactivation is believed to be due in a large part to the combined effects of a number of processing conditions, e.g., reaction temperature, reactant partial pressures, the phosphine ligand, the ligand to rhodium mole ratio, and rhodium concentration employed, which lead to the formation of inactive rhodium complex clusters. Since the variables significant for such catalyst instability are also variables essential for the hydroformylation, obviously such deactivation can not be totally avoided, although it can be controlled or minimized. However, eventually the activity of the catalyst will decrease to such a point that it is no longer desirable to operate the hydroformylation process, and the catalyst will either have to be reactivated or discharged and replaced with fresh catalyst. Accordingly, reactivation of such partially deactivated rhodium complex catalysts remains highly important to the state of the art in view of the high cost of rhodium, as seen by the many various methods that have been proposed by the prior art for minimizing or preventing such deactivation and/or reactivating the partially deactivated rhodium complex hydroformylation catalyst.

One of the more recent reactivation procedures, as disclosed in U.S. Pat. No. 4,861,918, resides in the treatment of the solubilized partially deactivated rhodium-tertiary organophosphine complex hydroformylation catalyst with various organic reagents, such as acetylenic compounds containing halogen, carboxylate, sulfonate or phosphonium radicals, to achieve a hydroformylation catalyst that is more chemically active than the initial partially deactivated catalyst starting material, said increase in reactivity exhibiting itself upon elimination from the treated catalyst product any hydroformylation catalytic inhibitor that might have been formed during the treatment procedure. However, while said treatment procedure has been found to be quite beneficial in restoring the activity of such partially deactivated rhodium catalysts, the heretofore proposed acetylenic reactant compounds, such as propargyl acetate, are for the most part not readily commercially available. Moreover such proposed acetylenic reactants due to their high functionality (i.e. acetylenic and salt groups) may be subject to various undesirable side reactions that may adversely affect the desired reactivation of the treated catalyst and/or its ultimate end use. Thus there is still a desire in the art for a method which would permit restoration of such partially deactivated rhodium catalyst activity with organic reagents that have greater commerical availability in comparison to the acetylenic compounds, such as propargyl acetate, disclosed in U.S. Pat. No. 4,861,918.

DISCLOSURE OF THE INVENTION

It has now been discovered that the activity of a rhodium-tertiary organophosphine complex hydroformylation catalyst that has become partially deactivated as a result of its employment in a hydroformylation reaction directed to producing aldehyde products by reacting an olefinic compound, carbon monoxide and hydrogen in the presence of a hydroformylation reaction medium containing a solubilized rhodium-tertiary organophosphine complex catalyst, can be improved by treating the solubilized partially deactivated rhodium-tertiary phosphine complex catalyst with propargyl alcohol and carboxylic acid, followed by elimination of such carboxylic acid from the treated catalyst solution.

Thus, it is an object of this invention to provide a process for improving the catalytic activity of such partially deactivated rhodium-tertiary organophosphine complex hydroformylation catalysts. Other objects and advantages of this invention will become readily apparent from the following description and appended claims.

Accordingly, a generic aspect of this invention can be described as a process for improving the catalytic activity of a partially deactivated solubilized rhodium tertiary organophosphine complex hydroformylation catalyst, which comprises (1) mixing under non-hydroformylating conditions, an organic liquid medium containing said solubilized partially deactivated complex catalyst, with propargyl alcohol and a carboxylic acid of the formula RCOOH wherein R represents hydrogen or an alkyl or aryl radical to obtain a treated solubilized rhodium-tertiary organophosphine complex product solution; and (2) eliminating from said product solution the carboxylic acid employed in Step (1), to obtain a rhodium-tertiary organophosphine complex hydroformylation catalyst that is more catalytically active than said partially deactivated rhodium-tertiary organophophine complex hydroformylation catalyst.

DESCRIPTION OF THE PREFERRED EMBODIMENTS

As noted above, the subject invention resides in the discovery that the catalytic activity of a rhodium-tertiary organophosphine complex hydroformylation catalyst which has become partially deactivated (via intrinsic deactivation) as a result of its continued employment in a hydroformylation reaction directed to producing aldehyde products by reacting an olefinic compound, carbon monoxide and hydrogen in the presence of a non-aqueous, homogeneous hydroformylation reaction medium containing solubilized rhodium-tertiary organophosphine complex catalyst can be improved by the process of this invention.

Thus, the solubilized partially deactivated rhodium-tertiary organophosphine complex catalyst contained in an organic liquid medium treated in accordance with this invention can be any such catalyst complex resulting from a non-aqueous, homogeneous hydroformylation process directed to producing aldehydes by hydroformylating an olefinic compound with carbon monoxide and hydrogen in the presence of a rhodium-tertiary organophosphine complex catalyst and which process has been operated to the extent that the originally employed catalyst complex has become at least partially deactivated, i.e. a catalyst which has become less reactive then its original counterpart. The extent of such catalytic deactivation (or catalyst activity) may be determined at any given time by comparing the hydroformylation conversion rate to aldehyde product based on such catalyst to the conversion rate obtained using fresh catalyst.

Moreover, the solubilized partially deactivated rhodium-tertiary organophosphine complex catalysts that may be reactivated in accordance with this invention can be present in any suitable organic liquid medium which would not unduly adversely affect the basic purpose of this invention. For example such organic liquid mediums may consist of only the partially deactivated rhodium-tertiary organophosphine complex catalyst and an organic solvent for said complex catalyst. More preferably such organic liquid mediums may comprise all or any part of the hydroformylation reaction medium and/or all or any part of the liquid catalyst recycle medium of the corresponding hydroformylation process that produced the partially deactivated rhodium-tertiary organophosphine complex catalyst.

As pointed out by the above, such methods for hydroformylating olefinic compounds to produce aldehydes with a rhodium-tertiary organophosphine complex catalyst are well known in the art. Thus it should be clear that the particular non-aqueous, homogeneous hydroformylation process for producing aldehydes from an olefinic compound, as well as the reaction conditions and ingredients of said hydroformylation process, which serve as a means for furnishing the solubilized partially deactivated rhodium-tertiary organophosphine complex catalyst containing organic liquid medium starting material of the present invention, are not critical features of the present invention.

In general, the hydroformylation processes comprise reacting an olefinic compound with carbon monoxide and hydrogen in a reaction vessel and in the presence of a non-aqueous hydroformylation reaction medium comprising aldehyde products, a solubilized rhodium-tertiary organophosphine complex catalyst, free tertiary organophosphine ligand and an organic solvent for said catalysts. In continuous hydroformylation reactions the aldehyde products are constantly being removed, the rhodium-tertiary organophosphine complex catalyst either remaining in the hydroformylation reaction medium in the reactor as in the case of a gas recycle operation (e.g., U.S. Pat. No. 4,247,486), or being recycled back to the reactor after removal of some of the liquid reaction medium from the reactor and separation of aldehyde product therefrom, as in the case of a liquid catalyst recycle operation (e.g., U.S. Pat. No. 4,148,830 and U.S. Pat. No. 4,731,486).

Thus the "organic liquid medium" starting material as employed herein means any non-aqueous, organic liquid medium comprising a partially deactivated rhodium-tertiary organophosphine complex hydroformylation catalyst, free tertiary organophosphine ligand, and an organic solvent for said complex catalyst and free ligand, and such liquid mediums may be derived from any conventional corresponding non-aqueous, homogeneous hydroformylation process. Moreover, the term "non-aqueous" as employed in this invention means a hydroformylation process that is conducted in the absence or essential absence of water, which is to say that any water, if present at all, in the hydroformylation reaction medium, is not present in an amount sufficient to cause either the process or said medium to be considered as encompassing a separate aqueous or water phase or layer in addition to an organic phase.

Accordingly, the organic liquid medium starting materials employable herein preferably contain at least some amount of three different main ingredients or components, i.e., the partially deactivated rhodium-tertiary organophosphine complex hydroformylation catalyst, free tertiary organophosphine ligand, and an organic solvent for said complex catalyst and said free ligand, said ingredients preferably corresponding to those employed and/or produced by the hydroformylation process from whence the organic liquid medium starting material may be derived.

Preferably, said organic liquid medium starting materials also contain at least some amount of the aldehyde product corresponding to the desired aldehyde product of the hydroformylation process from whence such organic liquid mediums may be derived, although it may be possible to remove all of such aldehyde product prior to treating the organic liquid medium by the process of this invention. Of course, it is to be further understood that the organic liquid medium starting materials of this invention can contain minor amounts of additional ingredients such as those which have either been deliberately employed in the hydroformylation process or formed in situ during said process. Examples of such additional ingredients that can also be present include unreacted olefin starting material, and in situ formed type products, such as unreacted isomerized olefin, hydrogenated olefin (e.g., corresponding saturated hydrocarbons or paraffin by-products); in situ type by-products derived from the aldehyde products, such as high boiling aldehyde condensation by-products (as described, e.g., in U.S. Pat. No. 4,148,830 and U.S. Pat. No. 4,247,486) and in situ type alkyl substituted phosphine ligand by-product (such as described, e.g., in U.S. Pat. No. 4,260,828).

Accordingly, it should be sufficient for the purpose of this invention to understand that, whatever compounds are present during the hydroformylation process from which the organic liquid medium starting materials of this invention can be derived, may also be correspondingly present in said organic liquid medium starting materials of this invention.

Thus, the particular partially deactivated rhodium tertiary organophosphine complex hydroformylation catalyst, present in the organic liquid medium starting material to be treated in accordance with this invention can be any such corresponding conventional rhodium hydroformylation catalyst which has been employed in the hydroformylation reaction to the extent that it has become partially deactivated (i.e., intrinsically deactivated). Accordingly, the particular partially deactivated rhodium-tertiary organophosphine complex hydroformylation catalyst, as well as its amount in a given organic liquid medium starting material of this invention, may obviously correspond to and merely be dependent upon the particular rhodium-tertiary organophosphine complex catalyst employed in and/or formed under the reaction conditions of the particular hydroformylation reaction from whence the organic liquid medium starting material to be treated according to this invention has been derived. For example illustrative rhodium-tertiary organophosphine complex catalysts and hydroformylation reactions, include, e.g., those disclosed in U.S. Pat. Nos. 3,527,809; 4,148,830; 4,247,486; 4,283,562; 4,400,548; 4,491,675; 4,593,127; 4,633,021; 4,716,250; 4,731,486; PCT Application, Publication No. WO 80/01690 (published August, 1980); and the like, the entire disclosures of which are incorporated herein by reference thereto. Of course, mixtures of different catalysts and organophosphine ligands can be employed if desired. Moreover, as noted in said references, the hydroformylation processes are generally and preferably carried out in the presence of free tertiary organophosphine ligand, i.e., ligand that is not complexed with the rhodium complex catalyst employed. While it is generally preferred that the free ligand be the same as the tertiary organophosphine ligand of the rhodium-tertiary organophosphine complex catalyst, such is not necessary. Accordingly it is to be understood that in the case of the rhodium-tertiary organophosphine complex catalyst, as well as in the case of the free tertiary organophosphine ligand, any conventional tertiary organophosphine ligand, heretofore advanced for such hydroformylation purposes, such as disclosed, e.g., by the above mentioned references, can be employed herein.

Accordingly, illustrative tertiary organophosphines that may be employed, either as the free ligand and/or as the ligand of the rhodium complex catalyst, include, e.g., trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl bisphosphines and bisphosphine mono-oxides, as well as ionic triorganophosphines containing at least one ionic moiety selected from the group consisting of the salts of sulfonic acid, of carboxylic acid, of phosphonic acid and of quaternary ammonium compounds, and the like. Of course any of the hydrocarbon radicals of such tertiary non-ionic and ionic organophosphines may be substituted, if desired, with any suitable substituent that does not unduly adversely affect the desired result of the hydroformylation process or this invention. Illustrative substituents that may be on the hydrocarbon radicals in addition of course to corresponding hydrocarbon radicals such as alkyl, aryl, aralkyl, alkaryl and cyclohexyl substituents, may include for example silyl radicals such as —Si($R^9$)$_3$; amino radicals such as —N($R^9$)$_2$; acyl radicals such as —C(O)$R^9$, acyloxy radicals such as —OC(O)$R^9$; amido radicals such as —CON($R^9$)$_2$ and —N($R^9$)CO$R^9$; sulfonyl radicals such as —SO$_2R^9$, alkoxy radicals such as —O$R^9$; thionyl radicals such as —S$R^9$, phosphonyl radicals such as —P(O)($R^9$)$_2$, as well as halogen, nitro, cyano, trifluoromethyl, hydroxy radicals, and the like, wherein each $R^9$ individually represents the same or different monovalent hydrocarbon radical having from 1 to 18 carbon atoms (e.g., alkyl, aryl, aralkyl, alkaryl and cyclohexyl radicals), with the proviso that amino substituents such as —N($R^9$)$_2$, each $R^9$ taken together can also represent a divalent bridging group that forms a heterocyclic radical with the nitrogen atom, and in amido substituents such as —C(O)N($R^9$)$_2$ and —N($R^9$)CO$R^9$ each $R^9$ bonded to N can also be hydrogen. Of course, it is to be understood that any of the substituted or unsubstituted hydrocarbon radicals groups that make up a particular given tertiary organophosphine may be the same or different.

Such tertiary organophosphines and corresponding rhodium-tertiary organophosphine complex catalysts and/or methods for their preparation are well known as seen, e.g., by the above mentioned references. Preferred tertiary organophosphines are non-ionic and ionic phosphines, such as non-ionic triorganophosphines having the formula ($R^{10}$)$_3$P wherein each $R^{10}$ individually represents a monovalent hydrocarbon radical containing from 1 to 18 carbon atoms selected from the alkyl, aralkyl, alkaryl, cycloalkyl and aryl radicals, as disclosed, e.g., in U.S. Pat. Nos. 3,527,809 and 4,283,562, and the like; and ionic triorganophosphines having the formula

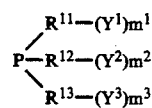

wherein $R^{11}$, $R^{12}$, and $R^{13}$ each individually represent a monovalent hydrocarbon radical containing from 1 to 18 carbon atoms selected from the group consisting of alkyl, aryl, alkaryl, aralkyl and cycloalkyl radicals, wherein $Y^1$, $Y^2$, and $Y^3$ each individually represent an ionic radical of overall neutral charge selected from the group consisting of —SO$_3$M, —PO$_3$M, and —COOM wherein M represents and inorganic (e.g., alkali or alkali earth metal) or organic (e.g., quaternary ammonium) radical, and —N($R^{13}$)$_3Y^4$ wherein each $R^{13}$ represents hydrogen or a monovalent hydrocarbon radical containing from 1 to 18 carbon atoms selected from the group consisting of alkyl, aryl, alkaryl, aralkyl and cycloalkyl radicals and wherein $Y^4$ represents an inorganic or organic anion; wherein $m^1$, $m^2$ and $m^3$ are integers each having a value of from 0 to 3, at least one of $m^1$, $m^2$, and $m^3$ having a value of at least one, as, e.g., in U.S. Pat. Nos. 4,633,021; 4,716,250; and 4,731,486; and the like, especially U.S. Pat. No. 4,731,486.

Among the more preferred tertiary organophosphines are triphenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, and tribenzylphosphine, as well as the alkali and alkaline earth metal salts of sulfonated triphenylphosphines, e.g., of (tri-m-sulfophenyl) phosphine and of (m-sulfophenyl) diphenyl phosphine and the like. The most preferred ligands are triphenylphosphine (TPP), and the sodium salt of 3-(diphenylphosphino)-benzene sulfonic acid (TPPMS-Na), while the most preferred catalysts are rhodium-TPP and rhodium-TPPMS-Na complexes.

As seen by the above mentioned hydroformylation references, the rhodium complex catalysts are generally considered as consisting essentially of rhodium complexed with carbon monoxide and tertiary organophosphine (generally corresponding to the free tertiary organophosphine ligand also normally present in the reaction medium). The catalyst terminology "consisting essentially of" is not meant to exclude, but rather include the possibility of other ligands or anions, complexed with the rhodium such as hydrogen which is also a ligand in addition to the carbon monoxide and tertiary organophosphine, the hydrogen being derived from the hydrogen gas of the hydroformylation reaction, if not already present in the catalyst precursor. Such hydroformylation catalysts may be formed in situ during the hydroformylation reaction or preformed by methods known in the art. For example, preformed rhodium hydridocarbonyl-tris (tertiary organophosphines) may be introduced into the reaction medium of the hydroformylation reaction. Alternatively, rhodium catalyst precursors such as rhodium carbonyl tertiary organophosphine acetylacetonates, $Rh_2O_3$, $Rh_4(CO)_{12}$, $Rh_6(CO)_{16}$, $Rh(NO_3)_3$ or rhodium dicarbonyl acetylacetonate, and the like, may be introduced into the reaction medium of the hydroformylation reaction. In any event, an active rhodium complex hydroformylation catalyst is present in the hydroformylation reaction medium under the conditions of hydroformylation.

However, it is to be noted that the successful practice of this invention does not depend and is not predicated on any explanation as to the exact structure or nature of the active rhodium complex catalyst species or as to the exact structure or nature of the partially deactivated rhodium hydroformylation catalyst species formed during the hydroformylation. Clearly, for the purpose of understanding this invention, it is sufficient to simply point out that the partially deactivated rhodium-tertiary organophosphine complex hydroformylation catalysts present in the liquid medium starting materials of this invention can be any such complex partially deactivated catalyst mixture resulting from the use of a corresponding rhodium-tertiary organophosphine complex catalyst in the hydroformylation reaction medium of the hydroformylation process from whence the particular organic liquid medium starting material employable in the process of this invention is derived.

The amount of the partially deactivated rhodium-tertiary phosphine complex hydroformylation catalyst present in the organic liquid medium starting materials of this invention may range from about one part per million (ppm), up to about 50,000 parts per million (ppm) or more, calculated as rhodium metal. In general, the amount of such partially deactivated rhodium complex catalyst present in the organic liquid medium starting material of this invention preferably corresponds to the amount of the rhodium-tertiary organophosphine complex hydroformylation catalyst employed in the hydroformylation reaction medium of the hydroformylation process from whence the organic liquid medium starting material may be derived, and such amounts are commonly expressed in terms of the amount of rhodium present calculated as rhodium metal. In the more preferred low pressure hydroformylation processes, rhodium hydroformylation concentrations preferably do not exceed 500 ppm, calculated as rhodium metal, with concentrations of from about 50 up to 300 ppm, calculated as rhodium metal being even more preferred. Of course, the organic liquid medium starting materials of this invention may contain higher concentrations of rhodium than present in the hydroformylation reaction medium, and such may be readily obtained, e.g., simply by concentrating the rhodium catalyst containing hydroformylation medium prior to employing same as the organic liquid medium starting material of this invention. Such concentration procedures, e.g., may range from merely removing some of the aldehyde product on up to preparing very viscous rhodium containing concentrates such as taught, e.g., in U.S. Pat. No. 4,297,239. Rhodium concentrations in the range of from about 5 to about 10,000 ppm, and more preferably from about 10 to about 1000 ppm, of rhodium, calculated as rhodium metal, should be sufficient for most hydroformylation process, and such corresponding amounts are preferably present in the organic liquid medium starting materials of this invention.

As noted above the tertiary organophosphine ligands defined herein are employed in this invention as both the ligand of the rhodium-tertiary organophosphine complex catalyst as well as the free tertiary phosphine ligand that is also present in the organic liquid medium starting materials of this invention. In a given situation such rhodium-phosphine complexes and free phosphine ligands of course will correspond to those employed in the hydroformylation process from which said organic liquid mediums may be derived. In addition. it is to be understood, that while the tertiary organophosphine of the rhodium complex catalyst and free tertiary organophosphine ligand present in the reaction medium of a given hydroformylation process are normally the same, different tertiary organophosphine ligands as well as mixtures of two or more different tertiary organophosphine ligands may be employed for each individual purpose, if desired. As in the case with the amounts of rhodium complex catalyst employed, the amount of free tertiary organophosphorus ligand present in a given organic liquid medium starting material of this invention will in general correspond to that amount of corresponding free ligand present in the hydroformylation process from which said organic liquid medium may be derived. For instance, since the hydroformylation process may be carried out in any excess amount of free tertiary organophosphine ligand desired, e.g., at least one mole of free tertiary organophosphine ligand per mole of rhodium present in the reaction medium, the amount of free tertiary organophosphine ligand present in a given organic liquid medium starting material of this invention can also be any corresponding excess amount, e.g., at least one mole of free tertiary organophosphine ligand per mole of rhodium metal present in the organic liquid medium starting material.

In general, an amount of free tertiary organophosphine ligand of from about 2 to about 300, and preferably from about 5 to about 200 moles per mole of rhodium metal present in the reaction medium should be suitable for most hydroformylation processes. Accordingly, corresponding amounts of free tertiary organophosphine ligand may be present in the organic liquid medium starting materials of this invention.

The organic liquid medium starting materials of this invention also contain an organic solvent generally corresponding to that employed for solubilizing the rhodium-tertiary organophosphine complex catalyst and free tertiary organophosphine ligand present in the reaction medium of the hydroformylation process from which said organic liquid medium starting materials of this invention may be derived. Any suitable solvent which does not adversely interfere with the intended process of this invention can be employed. Such solvents are well known in the art and encompass both polar and non-polar organic solvents. Illustrative suitable organic solvents include those described, e.g., in U.S. Pat. Nos. 3,527,809; 4,148,830; and 4,731,486. Of course, mixtures of one or more different solvents may be employed if desired. Moreover, when organic solvent soluble non-ionic tertiary organophosphine ligands are involved, the preferred solvents are aldehyde compounds corresponding to the aldehyde products of the hydroformylation process and/or higher boiling aldehyde condensation by-products such as described, e.g., in U.S. Pat. Nos. 4,148,830 and 4,247,486. When organic solvent soluble ionic tertiary organophosphine ligands are involved, such ligands generally contain only one ionic moiety. The preferred solvents are polar organic solubilizing agents selected from the group consisting of an alkylene oxide oligomer having an average molecular weight of at least 150, an organic nonionic surfactant mono-ol having an average molecular weight of at least 300 and a polar organic compound having a molecular weight of less than 150 and a Hildebrand solubility value of at least 10, as well as mixtures thereof, such as described, e.g., in U.S. Pat. No. 4,731,486. Preferred polar organic solvents for organic solvent-soluble ionic tertiary phosphine ligands and rhodium-ionic tertiary phosphine complex catalysts, are amides, sulfoxides and sulfones, and mixtures thereof, the more preferred polar organic solubilizing agents being amides, for instance, N-methylpyrolidone. The amount of organic solvent present in the organic liquid medium starting materials need only be that amount sufficient to solubilize the partially deactivated rhodium-tertiary organophosphine complex catalyst and free ligand present in said organic liquid medium. In general, such amounts of organic solvent may correspond to those amounts of organic solvent present in the reaction medium or catalyst containing recycle medium of the hydroformylation process from whence the organic liquid medium starting materials of this invention may be derived.

Thus, in general, the amount of organic solvent present in the organic liquid medium starting materials of this invention may range from about 5 to about 95 parts by weight based on the total weight of said organic liquid medium starting material. The preferred polar organic solvents for organic solvent soluble ionic tertiary organophosphines and rhodium-ionic tertiary organophosphine complex catalysts are preferably present in hydroformylation reaction mediums in an amount not greater than 60 percent by weight of said medium.

Finally, as noted above, the organic liquid medium starting materials of the process of this invention also preferably contain at least some amount of aldehyde product corresponding to the aldehyde product obtained by the hydroformylation process from whence said organic liquid medium starting materials may be derived. Such aldehydes may contain from 3 to 31 carbon atoms and encompass the corresponding hydroformylation aldehyde products obtained upon hydroformylating olefinic compounds containing from 2 to 30 carbon atoms. Such olefinic compounds can be terminally or internally unsaturated and be of straight-chain, branched chain or cyclic structures, as well as be olefin mixtures, such as obtained from the oligomerization of propene, butene, isobutene, etc., (such as so called dimeric, trimeric or tetrameric propylene, codibutylene, and the like, as disclosed, e.g., in U.S. Pat. Nos. 4,518,809 and 4,528,403). Moreover, such olefinic compounds may further contain one or more ethylenic unsaturated groups, and of course, mixtures of two or more different olefinic compounds may be employed as the starting hydroformylation material if desired. Further such olefinic compounds and the corresponding aldehyde products derived therefrom may also contain one or more groups or substituents which do not unduly adversely affect the hydroformylation process or the process of this invention such as described, e.g., in U.S. Pat. Nos. 3,527,809; 4,731,486 and the like.

Illustrative olefinic unsaturated compounds are alpha-olefins, internal olefins, alkyl alkenoates, alkenyl alkanoates, alkenyl alkyl ethers, alkenols, and the like, e.g., ethylene, propylene, 1-butene, 1-hexene, 1-octene, 1-nonene, 1-decene, 1-undecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-pentene, 2-hexene, 2-heptene, propylene dimers, propylene trimers, propylene tetramers, 2-ethyl hexene, 2-octene, styrene, 3-phenyl-1-propene, 1,4-hexadiene, 1,7-octadiene, 3-cyclohexyl-1-butene, allyl butyrate, methyl methacrylate, vinyl ethyl ether, vinyl methyl ether, allyl ethyl ether, n-propyl-7-octenoate, 3-butenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenyl-benzene, eugenol, iso-eugenol, safrole, iso-safrole, anethol, 4-allylanisole, indene, limonene, beta-pinene, dicyclopentadiene, cyclooctadiene, camphene, linalool, and the like.

Accordingly, illustrative aldehyde products include, e.g., propionaldehyde, n-butyraldehyde, isobutyraldehyde, n-valeraldehyde, 2-methyl-1-butyraldehyde, hexanal, 2-methyl valeraldehyde, heptanal, 2-methyl-1-hexanal, octanal, 2-methyl-1-heptanal, nonanal, 2-methyl-1-octanal, 2-ethyl-1-heptanal, 3-propyl-1-hexanal, decanal, 2-methyl-1-nonanal, undecanal, 2-methyl-1-decanal, dodecanal, 2-methyl-1-undecanal, tridecanal, 2-methyl-1-tridecanal, 2-ethyl-1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonadecanal, 2-methyl-1-octadecanal, 2-ethyl-1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl-1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Of course, it is understood that the aldehyde product of an alpha olefin will normally be a mixture of the normal straight chain aldehyde and its branched chain aldehyde isomer obtained upon hydroformylating said olefin. Moreover, mixtures of totally different aldehyde products can be present in the organic liquid medium starting materials employable in this invention, e.g., when such organic liquid mediums are derived from a process that hydroformylates mixtures of totally different olefinic compounds, such as, e.g., mixtures of alpha olefins and internal olefins or mixtures of two different alpha olefins. The preferred aldehyde products present in the hydroformylation reaction product compositions employable in this invention are those derived from hydroformylating alpha olefins, internal olefins and mixtures of such alpha and internal olefins.

The more preferred olefin starting materials are alpha olefins having from 2 to 20 carbon atoms and more preferably from 3 to 14 carbon atoms. Of course it is to be understood that commercial alpha olefins containing 4 or more carbon atoms may contain minor amounts of corresponding internal olefins and/or their corresponding saturated hydrocarbon and that such commercial olefins need not necessarily be purified from same prior to being hydroformylated.

The amount of aldehyde product present in the organic liquid mediums employable as the starting materials of this invention may range from 0 to about 90 percent by weight or higher of the organic liquid medium. Such amounts will, in general, be dependent upon the particular reaction conditions and efficiency of the hydroformylation process from whence the organic liquid medium starting materials of this invention may be derived. Preferred hydroformylation processes are those capable of producing a hydroformylation reaction product medium containing from about 10 to about 80 percent by weight of aldehyde product. Preferably, the amount of aldehyde product present in the organic liquid medium starting materials employable in this invention may range of from 0 to about 80 percent by weight, and more preferably from about 30 to 70 percent by weight, of the organic liquid medium. Moreover, when Step (2) of the process of this invention involves phase suparation between organic and aqueous liquid phases, said organic liquid medium starting materials preferably contain at least about 30% and most preferably at least about 45% by weight of aldehyde in order to facilitate said phase separation and prevent emulsion formation.

More preferably, the organic liquid medium starting materials of this invention correspond to all or a part of the reaction medium of a hydroformylation process as outlined herein or correspond to all or a part of the organic liquid catalyst containing recycle medium of such a hydroformylation process (i.e., that organic liquid catalyst containing residue obtained, after the removal of that desired amount of aldehyde product from the hydroformulation reaction product medium outside of the hydroformulation reactor or hydroformylation zone), which is recycled to the reactor in order to establish a continuous hydroformylation catalyst recycle process.

Of course, it is to be further understood that the organic liquid medium starting materials of this invention may also contain additional ingredients corresponding to those which have either been deliberately employed in the hydroformylation process from which said organic liquid medium starting materials may be derived or which have been formed in situ during the hydroformylation process. For instance, obviously since an olefin starting material is being hydroformylated, the organic liquid medium starting materials of this invention may contain some unreacted olefin starting material. The amount of such unreacted olefin present in any said organic liquid medium starting material will be in general governed by the efficiency of the hydroformylation process. In general, amounts of unreacted olefin may range from about 0 to about 20 percent by weight of the organic liquid medium.

Likewise, minor amounts of in situ type by-products that may be formed during the hydroformylation process may also be correspondingly present in the organic liquid medium starting materials of this invention, e.g., in situ type by-products derived from the olefinic starting materials, such as unreacted isomerized olefin, hydrogenated olefin (e.g., corresponding saturated hydrocarbons or paraffin by-products); in situ type by-products derived from the aldehyde products, such as high boiling aldehyde condensation by-products (as described, e.g., in U.S. Pat. No. 4,148,830 and said U.S. Pat. No. 4,247,486 discussed above); and possibly even some in situ type alkyl substituted phosphorus ligand by-product. Further minor amounts of other additional co-solvent type diluents or additives, if employed in the hydroformylation process may correspondingly be present in the organic liquid medium starting materials of this invention. Accordingly, it should be sufficient for the purpose of this invention to understand that whatever compounds are present in the hydroformylation reaction medium of the hydroformylation process from which the organic liquid medium starting material of this invention is derived, may also be correspondingly present in said organic liquid medium starting materials.

Likewise, the reaction conditions for effecting such hydroformylation processes may be those heretofore conventionally used and may comprise a reaction temperature of from about 45° C. to about 200° C. and pressures ranging from about 1 to 10,000 psia.

The total gas pressure of hydrogen, carbon monoxide and olefinic unsaturated starting compound of such hydroformylation processes may range from about 1 to about 10,000 psia, while it is preferred that the process be operated at a total gas pressure of hydrogen, carbon monoxide and olefinic unsaturated starting compound of less then about 1500 psia and more preferably less than about 500 psia. The partial pressure of the reactants is not particularly critical and depends predominately on the amount and nature of the reactants employed and the desired result to be obtained. For instance, in hydroformylation processes the carbon monoxide partial pressure is preferably from about 1 to about 120 psia and more preferably from about 3 to about 90 psia, while the hydrogen partial pressure is preferably about 10 to about 200 psia and more preferably from about 20 to about 160 psia. In general, the $H_2$:CO molar ratio of gaseous hydrogen to carbon monoxide may range from about 1:10 to 100:1 or higher, the more preferred hydrogen to carbon monoxide molar ratio being from about 1:1 to about 10:1. Further, it is more preferred to employ a hydroformylation reaction temperature of from about 60° C. to about 140° C. Moreover, the subject invention is especially useful for improving continuous hydroformylation processes.

It is to be further understood that while the subject invention is preferably directed to treating an organic liquid medium that has been directly obtained from a hydroformylation process, the organic liquid medium starting materials of this invention also encompass any subsequent organic liquid medium derived from such an initial organic liquid medium so obtained, provided said subsequently derived organic liquid medium also contains at least some amount of each of the three main ingredients defined above i.e., catalyst, the partially deactivated rhodium-tertiary organophosphine complex catalyst, the free tertiary organophosphine ligand and an organic solvent for said complex catalyst and said free ligand, and more preferably also at least some amount of the aldehyde product.

As noted above, Step (1) of the process of this invention involves treating the solubilized partially deactivated complex catalyst contained in the organic liquid medium starting material with propargyl alcohol and a carboxylic acid compound of the formula

R—COOH wherein R represents hydrogen or an alkyl or aryl radical, such as, e.g., an alkyl radical containing from 1 to 4 carbon atoms or a phenyl radical. Illustrative carboxylic acid compounds include, e.g., formic acid, acetic acid, propionic acid, n-butyric acid, isobutyric acid and benzoic acid. Of course, if desired such carboxylic acids may be substituted with one or more substituents that do not unduly adversely affect the desired purpose of this invention, e.g., a cyano radical as in cyanoacetic acid. While, in general, it is preferred to employ a single carboxylic acid, mixtures of such carboxylic acids may be employed if desired. Preferably R represents hydrogen or an alkyl radical, the most preferred carboxylic acid compound being acetic acid.

More particularly, the treatment of the organic liquid medium starting material of this invention (i.e. Step 1), which is conducted under non-hydroformylation conditions, i.e., in the essential absence of syn gas ($CO+H_2$), can be accomplished by mixing the propargyl alcohol and carboxylic acid compound of choice with the desired organic liquid medium starting material to obtain a treated solubilized rhodium-tertiary organophosphine complex product solution. The manner of said mixing of the propargyl alcohol and carboxylic acid with the organic liquid medium starting material is not critical and such can be carried out in any conventional fashion using any suitable equipment and technique, the preferred result merely being a thorough inclusion of the propargyl alcohol and carboxylic acid in the organic liquid medium. Merely adding the propargyl alcohol and carboxylic acid to the organic liquid medium and gently stirring the solution should be sufficient to accomplish the desired result. If desired, the propargyl alcohol and carboxylic acid may be premixed or added to the organic liquid medium starting material simultaneously or in any order. In general, it is preferred to add the carboxylic acid first, followed by the addition of the propargyl alcohol.

Moreover, in view of the fact that the subject invention is directed to obtaining at least some improvement in the hydroformylation activity of the partially deactivated rhodium-tertiary organophosphine complex hydroformylation catalyst contained in the organic liquid medium to be treated and because the partially deactivated catalysts in said organic liquid medium starting materials can vary both in terms of their nature and concentrations it is apparent no specific values can be arbitrarily given to such treatment conditions as, e.g., the amount of propargyl alcohol and carboxylic acid, pressure, temperature and contact time for said treatment, that will encompass every given situation. Such conditions can vary greatly (are not narrowly critical) and obviously need only be at least sufficient to obtain the result desired. For instance, in some cases smaller amounts of the propargyl alcohol and carboxylic acid may be beneficial, while in other circumstances larger amounts of the propargyl alcohol and carboxylic acid may prove more desirable. Likewise, treatment conditions such as temperature, pressure and contact time may also vary greatly and any suitable combination of such conditions may be employed herein. For instance, a decrease in any one of such conditions may be compensated for by an increase in one or both of the other conditions, while the opposite correlation is also true. In general, the propargyl alcohol and carboxylic acid may be added to and mixed with the organic liquid medium starting material at organic liquid temperatures ranging from about 10° C. to about 180° C., while temperatures ranging from about 20° C. to about 140° C. may be suitable in most instances. It is generally preferred to carry out said treatment at atmospheric (ambient) pressure, although higher or lower pressures may be employed if desired. Of course, it is obvious that the contact time of the propargyl alcohol and carboxylic acid with the organic liquid medium involved will be directly related to the particular partially deactivated rhodium-tertiary organophosphine complex catalyst involved, as well as to such treatment conditions such as temperature, etc., and such contact time may vary from a matter of minutes to several hours. Experience will determine the preferred temperature and contact time. Lower temperatures, e.g. 90° C. or below may be preferred.

However, said treatment of the organic liquid medium starting material with the propargyl alcohol and carboxylic acid of this invention must be under non-hydroformylation conditions, which is to say that Step (1) of the process of this invention must be carried out in the essential absence of syn gas ($CO+H_2$), thus preventing any adverse simultaneous hydroformylation in the organic liquid medium during said Step (1). Preferably, said Step (1) is carried out under a nitrogen atmosphere, although mixtures of nitrogen and any other gas (except syn gas) may be employed provided they do not unduly adversely affect the desired purpose of this invention. For example, hydrogen may be employed.

As noted, the amounts of propargyl alcohol and carboxylic acid employed in Step (1) of this invention need only be that minimum amount necessary to help achieve the desired end result of this invention. In general, it is considered that the amount of propargyl alcohol and carboxylic acid employed may each range from about 0.1 up to about 1000 moles or higher per mole of rhodium, calculated as rhodium metal, in the organic liquid medium starting material, although it is recommended to employ at least one mole of each of the propargyl alcohol and carboxylic acid per mole of said rhodium. More preferably, it is recommended that an excess molar amount of each of the propargyl alcohol and carboxylic acid be employed, although no added benefit is seen in employing very large excess amounts. Indeed very large excess amounts could be more detrimental than positive. In general, it is considered that amounts of each of the propargyl alcohol and carboxylic acids ranging from about 0.5 to 500 moles per mole of rhodium, calculated as rhodium metal, in the organic liquid starting material should be sufficient for most purposes, with preferred amounts being from about 1 to about 300 moles of each of the propargyl alcohol and carboxylic acid per mole of rhodium, calculated as rhodium metal. At the same time, in general, the molar ratio of propargyl alcohol to carboxylic acid employed may range from about 4:1 to 1:4. A slight excess of carboxylic acid relative to propargyl alcohol may be preferred, although very good results have been obtained employing a molar ratio of propargyl alcohol to carboxylic acid of about 1:1.

In any event, it is sufficient for the purpose of this invention to understand that the propargyl alcohol and carboxylic acid are mixed with the organic liquid medium starting material in Step (1) of this invention to obtain a treated solubilized rhodium-tertiary organophosphine complex product solution, which in turn can be treated according to Step (2) of this invention to obtain a rhodium-tertiary organophosphine complex hydroformylation catalyst having better catalytic hydroformylation activity than the partially deactivated rhodium-tertiary organophosphine complex hydroformylation catalyst in said organic liquid medium starting material.

Step 2 of the process of this invention comprises removing the carboxylic acid employed in Step (1) from the treated solubilized rhodium-tertiary organophosphine complex product solution of Step (1).

For instance, while not intending to be held to any specific chemical theory or mechanistic discourse on just exactly how the beneficial desired result of the process of this invention is achieved, it is considered that intrinsic deactivation of the rhodium-tertiary organophosphine catalyst is due at least in part to the in situ formation of rhodium complex clusters during the hydroformylation process, which are catalytically inactive or less active than the active rhodium complex catalyst species, thus decreasing the amount of active rhodium values in the hydroformylation reaction medium. It is further considered that in Step (1) of the process of this invention the propargyl alcohol reacts with the rhodium to break up the undesirable rhodium clusters into new smaller monomeric rhodium complex species of active rhodium values. However, the propargyl alcohol, when employed alone, also has a strong propensity to be immediately oligomerized into polymeric materials. This undesirable side reaction reduces the amount of propargyl alcohol available for use in breaking up the inactive rhodium clusters, thereby detrimentally affecting the desired reactivation of the catalyst. It has now been found that the use of a carboxylic acid along with the propargyl alcohol in Step (1) of this invention prevents or at least greatly minimizes said oligomerization side reaction of the propargyl alcohol, thereby helping to maximize its effectiveness in breaking up said inactive rhodium clusters and reactivating the catalyst. It is theorized that the carboxylic acid employed quickly complexes with the monomeric rhodium species that result from the breaking up of such rhodium clusters to temporarily form a less active rhodium complex that is not so prone to catalyzing the oligomerization of the propargyl alcohol. It is further believed that such rhodium-carboxylic acid complexes help prevent the rhodium values from reclustering.

In any event, the new rhodium complex species in the treated solubilized rhodium-tertiary organophosphine complex product solution of Step (1) does not immediately exhibit improved catalytic activity over that of the partially deactivated rhodium-tertiary organophosphine complex catalyst starting material, and such is considered to be due to the carboxylic acid employed in said Step (1) treatment, be it present in its free form and/or as part of the new rhodium complex species formed by the treatment of Step (1).

It has also been found that elimination (removal) of the carboxylic acid, in whatever form it is present as, results in the obtaining of a rhodium-tertiary organophosphine complex hydroformylation catalyst that is more catalytically active than the partially deactivated rhodium-tertiary organophosphine complex hydroformylation catalyst starting material of the process of this invention. Again, while not intending to be held to any specific chemical theory or mechanistic disclosure as to the actual working of this invention, it is considered that during and/or as a result of the removal of such carboxylic acid via Step (2), the treated solubilized rhodium complex product of Step (1) is converted from an inhibited complex to an active rhodium complex species. In any event, it is sufficient for the purpose of understanding this invention to know that as a result of both Step (1) and Step(2) of the process of this invention, a rhodium-tertiary organophosphine complex hydroformylation catalyst is obtained that is more catalytically active than the partially deactivated rhodium-diorganophosphine complex hydroformylation catalyst present in the organic liquid medium starting material.

Accordingly, Step (2) of the process of this invention comprises removing the carboxylic acid employed in Step (1) from the treated solubilized rhodium-tertiary organophosphine complex product solution of Step (1) to obtain a rhodium-tertiary organophosphine complex hydroformylation catalyst that is more catalytically active, than the partially deactivated rhodium-tertiary organophosphine complex hydroformylation catalyst in the organic liquid medium of Step (1). Said removal of such carboxylic acid by Step (2) of the process of this invention may be carried out as described more fully below.

The preferred procedure of said Step (2) comprises removing such carboxylic acid employed in Step (1) by contacting the treated organic solvent-solubilized rhodium-tertiary organophosphine complex product of Step (1) with an aqueous solution containing a tertiary alkanolamine and phase separating the organic and aqueous phases of the resultant mixture to obtain an organic solubilized rhodium-tertiary organophosphine complex hydroformylation catalyst product that is more catalytically active than the organic solubilized partially deactivated rhodium-tertiary organophosphine complex hydroformylation catalyst contained in the organic liquid medium starting material of Step (1).

More specifically, this preferred procedure of Step (2) may be described as a process consisting essentially of (a) mixing under non-hydroformylation conditions, the treated rhodium-tertiary organophosphine complex product solution of Step (1), with an aqueous solution containing from about 1 to about 25 percent by weight of a tertiary alkanolamine to form a water-soluble salt between said tertiary alkanolamine and the carboxylic acid;

(b) allowing the resulting mixture to settle into two distinct liquid phases;

(c) separating the aqueous phase which contains said salt from the organic phase containing the rhodium-tertiary organophosphine complex hydroformylation catalyst resulting from steps (a) and (b); and (d) washing said non-aqueous organic phase of step (c) with water, to obtain an organic solubilized rhodium-tertiary organophosphine complex hydroformylation catalyst that is more catalytically active than the partially deactivated rhodium-tertiary organophosphine complex hydroformylation catalyst starting material of Step (1).

The improvement in hydroformylation catalytic activity of the obtained rhodium-tertiary organophosphine complex product may then be confirmed by employing same in a non-aqueous hydroformylation process. Of course it is to be understood that such confirmation of improved catalytic activity may or may not be immediately obtained upon the start up of such a non-aqueous hydroformylation process but may come about later, after the hydroformylation has been continuously carried out for a while.

Another procedure of Step (2) merely comprises employing the treated rhodium-tertiary organophosphine complex product solution of Step (1) in a continuous hydroformylation process until a rhodium-tertiary organophosphine complex hydroformylation catalyst is obtained that is more catalytically active than the solubilized partially deactivated rhodium-tertiary organophosphine complex hydroformylation catalyst contained in the organic liquid starting material of Step (1). For example, it is considered that the carboxylic acid employed in Step (1) may be gradually eliminated (removed) from the reaction medium of the continuous hydroformylation process, e.g., via the distillation recovery procedure used to obtain the desired aldehyde product, thus resulting in the desired catalytically improved rhodium-tertiary organophosphine complex catalyst. Said improvement in catalytic activity may be readily determined by analyzing for same during said continuous hydroformylation. However, depending upon the amount and boiling point of the carboxylic acid employed in Step (1), such confirmation of improved activity may only be exhibited after the hydroformylation has been continuously carried out for a while. Obviously, larger amounts and/or higher boiling carboxylic acids will take longer to be removed in this manner.

The subject invention is preferably directed to improving the catalytic activity of a partially deactivated rhodium-tertiary organophosphine complex hydroformylation catalyst that has been derived from a non-aqueous hydroformylation process for reuse in the same or similar non-aqueous hydroformylation process and removing the carboxylic acid employed in Step (1) from the treated product solution of Step (1) by employing an aqueous solution of a tertiary alkanol amine in Step (2) of the process of this invention.

As pointed out above, an aqueous solution of 1 to 25 percent by weight of a tertiary alkanolamine can be employed to remove the carboxylic acid via Step (2) of the process of this invention. Such tertiary alkanolamines include those of the formula

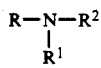

wherein R is a hydroxyalkyl radical containing from 2 to 4 carbon atoms; and wherein $R^1$ and $R^2$ are each individually selected from the group consisting of alkyl radicals containing from 1 to 4 carbon atoms, hydroxyalkyl radicals containing from 2 to 4 carbon atoms, and a phenyl radical. The more preferred tertiary alkanolamines are trialkanolamines (i.e., wherein each R, $R^1$ and $R^2$ group is a hydroxyalkyl radical containing from 2 to 4 carbon atoms). Illustrative tertiary alkanolamines include triethanolamine, triisopropanolamine, tri-sec-butanolamine, diethylethanolamine, dimethylethanolamine, dibutylethanolamine, phenylethylethanolamine, methyldiethanolamine, ethyldiethanolamine, phenyldiethanolamine, dimethylisopropanolamine, diisopropanolethanolamine, and the like. Of course, the aqueous tertiary alkanolamine solution employable herein may contain a mixture of two or more of such tertiary alkanolamines, if desired. The most preferred tertiary alkanolamine is triethanolamine.

Thus Step (2) of the process of this invention preferably consists essentially of mixing the treated product solution of Step (1) as defined above, with the aqueous solution of tertiary alkanolamine, allowing the mixture thereof to settle into two distinct phases and separating the aqueous (bottom) phase which contains the correspondingly produced water soluble salts of the tertiary alkanolamine and carboxylic acid, from the organic (top) phase containing the solubilized rhodium-tertiary organophosphine complex catalyst and the remainder of the organic liquid medium starting material, e.g., the aldehyde product, the free organophosphine ligand, and the higher boiling aldehyde condensation by-products, followed by washing said organic phase so obtained to further remove any minor amounts of the tertiary alkanolamine and/or said produced amine salts, that might have been left behind in the organic liquid medium, prior to reusing the obtained solubilized reactivated rhodium-tertiary organophosphine complex catalyst solution in a restarted or new hydroformylation process.

More particularly, said aqueous tertiary alkanolamine treatment is conducted under non-hydroformylation conditions, which is to say that it is carried out in the essential absence of syn gas. Preferably, it is carried out under a nitrogen atmosphere, although mixtures of nitrogen and any other gas (except syn gas) may be employed, provided that such does not unduly adversely affect the desired purpose of this invention. Such is preferably accomplished by merely mixing the aqueous solution of tertiary alkanolamine with the treated organic solvent-solubilized rhodium tertiary organophosphine complex product solution of said Step (1) outlined above, to produce water-soluble salts of said tertiary alkanolamine and whatever carboxylic acid is present in said treated product solution. Said mixing of the aqueous solution of tertiary alkanolamine with the treated product solution of said Step (1) can be carried out in any conventional fashion using any suitable equipment and technique, the preferred result merely being a thorough inclusion of the tertiary alkanolamine in the treated product solution so as to produce as much of such water-soluble salt products between said tertiary alkanolamine and carboxylic acid as possible. In general, merely adding the aqueous solution of tertiary alkanolamine to the treated product solution and gently agitating or stirring the solutions should be sufficient to accomplish the desired result. Of course, too vigorous a mixing is to be avoided since such might contribute to undesirable emulsion formation, which in turn can prevent and/or unduly adversely hinder the desired phase separation of the aqueous and organic phases. In general, said aqueous tertiary alkanol amine treatment may be carried out at liquid temperatures ranging from about 10° C. to about 150° C., and more preferably from about 40° C. to about 100° C., while temperatures ranging from about 45° C. to about 75° C. are most preferred. It is further generally preferred to carry out said treatment at atmospheric (ambient) pressure, although higher or lower pressures may be employed if desired. It should be noted that the higher the temperature the greater the chance for causing undesirable increased aldehyde condensation by-product formation, while the lower the temperature the greater the risk of undesirable emulsion formation due to increased solubility between the aldehyde and water. Accordingly, if it is found that emulsion formation is beginning to occur during Step (2) of the process of this invention, such may be abated by adding more aldehyde to the treated product solution. Of course, it is obvious that the contact time of the aqueous tertiary alkanolamine solution and the treated product solution involved may vary from a matter of minutes to a few hours. Experience will determine the most preferred temperature and contact time.

The tertiary alkanolamine concentration in the aqueous solution employable in Step (2) of the process of this invention need only be that minimum amount necessary to help achieve at least some improvement in the hydroformylation activity of the partially deactivated rhodium-tertiary organophosphine complex catalyst starting material. Preferably, the amount of tertiary alkanolamine employed will be sufficient to neutralize (form a salt with) at least 10 percent, and more preferably theoretically all, of the carboxylic acid present in the treated product solution of Step (1). In general, aqueous solutions containing from about 1 to 25 percent by weight of the tertiary alkanolamine should be sufficient for most purposes, with aqueous solutions containing from about 4 to about 15 percent by weight of the tertiary alkanolamine being preferred.

While from about 0.5 to 20 volume equivalents of said treated product solution starting material of Step (2) per volume equivalent of the aqueous solution of tertiary alkanolamine may be used, in general, it is preferred to employ organic to aqueous liquid ratios of from about 1 to about 5 volume equivalents, and more preferably from about 1 to about 3 volume equivalents, of said treated product solution starting material per volume equivalent of the aqueous solution of tertiary alkanolamine.

Said aqueous tertiary alkanolamine treatment further consists of allowing the resultant solution mixture to settle into two distince liquid phases, i.e., an organic (top) phase containing the catalyst, aldehyde and other non-water soluble ingredients of the organic liquid medium starting material, and an aqueous (bottom) phase containing the produced water-soluble salts of tertiary alkanolamine and carboxylic acid that was present in the treated product solution starting material. The settling time necessary for said phase separation has no effect on the activity of the catalyst and is dictated only by the ease with which the organic and aqueous phases undergo such separation. Preferably such separation should be completed within a day's time, and more preferably within a matter of a few hours or only minutes.

The physical separation of said aqueous and organic phases may be accomplished by any suitable conventional means, such as by draining off the bottom layer or decanting off the top layer, and the like.

The obtained resultant organic phase of said aqueous tertiary alkanolamine treatment is then washed with water, so as to remove any residual amounts of tertiary alkanolamine and/or said produced amine salts, that might have been left behind in the organic phase. Said water wash may be carried out in any conventional manner and suitable fashion. Ordinary tap water may be employed although deionized or distilled water or steam condensate is preferred. Said aqueous washing procedure is also carried out under non-hydroformylation conditions and under an inert atmosphere. Preferably, an organic liquid to water volume ratio of about 1 to 5, and more preferably about 1 to 3, volume equivalents of the organic liquid per volume equivalent of water is employed. Moreover said water wash is preferably conducted under atmospheric (ambient) pressure and at a liquid temperature of about 40° C. to about 100° C. and more preferably from about 45° C. to about 75° C. Thus it may be preferred to heat the obtained organic medium following the aqueous tertiary alkanolamine treatment in order to achieve such recommended temperatures for said water wash. Alternatively, hot water or steam condensate could be used for the wash. The recovery of the organic phase of said water wash containing a solubilized rhodium-tertiary organophosphine complex hydroformylation catalyst that is more catalytically active than the initial partially deactivated rhodium-tertiary organophosphine complex hydroformylation catalyst starting material of the process of this invention may be accomplished in the same manner as described above for the aqueous tertiary alkanolamine treatment. For instance, following a suitable mixing period the aqueous and organic layers are allowed to phase separate (settle), and the two liquid layers removed from each other by draining off the bottom phase and/or decantating off the top phase.

Repeated water washings, while possible, are considered unnecessary and in general only a single such water wash is recommended. Indeed, repeated water washings in the practice of this invention may serve only to increase the risk of undesirable emulsion formation.

Thus it should be clear, that while the selection of the optimum conditions of this invention to achieve the best results will be dependent upon one's experience in the utilization of the subject invention, in view of the disclosure and examples of this specification, only a certain measure of routine experimentation should be necessary in order to ascertain those conditions which are optimum for a given situation. Moreover, it should also be clear that one of the beneficial factors involved in this invention as employed herein is the wide processing latitude that one has in selecting the proper combination of conditions that will be most useful in obtaining or at least best approaching a particular desired result or need.

The improved regenerated hydroformylation catalytic activity of a rhodium complex catalyst obtained according to this invention may be determined by any suitable method such as, e.g., by measuring the rates of reaction of the partially deactivated rhodium complex catalyst in the organic liquid medium starting material of Step (1) and the reactivated rhodium complex catalyst obtained according to this invention as compared to the activity of a fresh rhodium complex catalyst (i.e., undeactivated catalyst) employed in the same manner. This effect may be easily determined by carrying out the hydroformylation reactions and by continuously monitoring the rate of hydroformylation. The difference in hydroformylation rate (or difference in catalyst activity) may then be observed in a convenient laboratory time frame, such as in terms of gram-moles per liter-hour of aldehyde product produced.

Thus, the process of this invention provides an excellent means for improving the hydroformylation catalytic activity of a solubilized rhodium-tertiary organophosphine complex hydroformylation catalyst which has become partially deactivated as a result of intrinsic deactivation, e.g., by treating all or part of the hydroformylation reaction medium of such a process or all or part of the catalyst complex containing liquid recycle medium of such process.

For instance, a particularly preferred and beneficial aspect of this invention may comprise merely stopping a rhodium-tertiary organophosphine catalyzed continuous hydroformylation reaction and treating the hydroformylation reaction medium derived therefrom according to the process of this invention, while said reaction medium remains in the hydroformylation reactor, to obtain the desired reactivated hydroformylation catalyst that is more catalytically active than the partially deactivated catalyst contained in said starting reaction medium. The hydroformylation reaction can obviously be stopped by any convenient method, e.g., by merely stopping the feed of the reactant gases (olefin, carbon monoxide and hydrogen) to the reaction vessel, allowing the residual reactants contained therein to react to completion, and shutting down the reaction being conducted in the reaction vessel. The recycle lines of the continuous reaction system can than be cleared in any conventional manner, and the derived hydroformylation medium treated according to the process of this invention. If a reactor or reaction vessel is essentially completely full of the liquid aldehyde product containing hydroformylation reaction medium, it may be necessary to first reduce the volume of the organic liquid medium in the reactor by removing some of the aldehyde product in order to accommodate the liquid volume of the aqueous solution of tertiary alkanolamine employed in the process of this invention. Such may be accomplished by stripping out whatever amount of aldehyde is desired from the reactor after the feed gases have been shut down. When done, however, it is recommended to leave a substantial aldehyde concentration in the medium. For instance, it is recommended to avoid concentrations of said organic liquid hydroformylation reaction mediums which would result in aldehyde concentrations of below 30 percent, since experience has indicated that, as the aldehyde concentration in the organic liquid medium starting material decreases, the ease of phase separation between the organic and aqueous layers also decreases, while the risk of emulsion formation increases. In general, concentration of an organic liquid hydroformylation medium in a full reactor down to about 70 percent should be suitable for most instances. Of course, if the reactor vessel is not essentially full of the liquid aldehyde product containing hydroformylation reaction medium and can directly accommodate a suitable amount of the aqueous tertiary alkanolamine, it may not be necessary to concentrate the hydroformylation reaction medium at all. The aqueous solution of tertiary alkanolamine which is preferably made up in a separate vessel and analyzed to ensure avoiding such possible contaminates as iron, halide, alkali metal and primary and secondary alkanolamines, may be added to the propargyl alcohol-carboxylic acid treated product solution of Step (1) in the reactor in any conventional suitable manner such as by pressuring the aqueous tertiary alkanolamine solution into the reactor from a suitable pressurized bomb. Following the addition of the aqueous solution of tertiary alkanolamine, the reactor solutions are gently agitated to provide sufficient mixing of the two phases to achieve one theoretical stage. Reaction of carboxylic acid with the aqueous alkanolamine solution is fast. Agitating the reaction mixture for about one hour should be adequate for most purposes. After mixing, the mixture is allowed to separate into two distinct liquid phases. The aqueous phase will settle to the bottom of the reactor vessels and may be drained from any suitable accessible low point in the reaction process. As the aqueous layer is removed, it should be retained in the unlikely event that it contains a higher than expected rhodium concentration. It is recommended that the solution be visually monitored to determine when the aqueous layer has been completely removed from the reactor vessels and the organic solution begins to drain. Liquid level detectors may also be useful to determine when the interface is approaching the drain valve, but close visual monitoring is preferred. The aqueous layer may have a cloudy, milky white appearance, while the reactivated organic catalyst solution may be brown. In order to remove residual portions of the tertiary alkanolamine and the amine salts from the reactivated catalyst containing organic solution, said organic solution may be washed with water as described above, in the same reactor vessels. Before the entire aqueous phase of said wash treatment is removed from the reactor, it is recommended to measure a sample of same for rhodium content in order to prevent an inadvertent loss of rhodium due to inadequate settling time. Minor amounts of rhodium in the aqueous phases of the recovered tertiary alkanolamine and water washes may be reclaimed by extracting the rhodium therefrom with the addition of an aldehyde such as butyraldehyde.

No special precautions need be considered for re-startup of the continuous hydroformylation reaction using the obtain reactivated catalyst solution in the reactor. Possible further minor amounts of water and/or tertiary alkanolamine left in the reactor vessels after the process of this invention are of no major concern as noted above. Such may be gradually stripped out of the restarted hydroformylation via an aldehyde product vaporizer.

Unlike some prior art reactivation procedures that require the addition of make-up quantities of active rhodium catalyst, solvent and/or triarylphosphine before reutilizing their treated catalyst, the subject inventive process is unique in that, since the treatment of this invention can be carried out in the same reaction vessel of the hydroformylation reaction, one need only turn back on the feed of olefinic compound, hydrogen and carbon monoxide to the treated hydroformylation reaction medium of this invention and restart the continuous hydroformylation reaction without the need of adding additional reaction medium components before restarting the reaction. Moreover, if one is using more than one reaction vessel in conjunction with the continuous hydroformylation reaction, one need not shut off the reaction being conducted in every reaction vessel, but only the reaction that is being conducted in that reaction vessel in which the derived hydroformylation medium is to be treated. Alternatively, it is to be understood that if desired, one could remove the entire hydroformylation reaction medium to be treated according to this invention from the reaction vessel of the hydroformylation reaction to a different vessel and then treat all or a proportionate part of said medium in said different vessel as desired. Such an optional procedure allows one to employ the empty hydroformylation reaction vessel for any other type of purpose such as for hydroformylating a different olefinic compound than employed in the initial hydroformylation reaction from which the medium to be treated has been derived. This would allow one to store the medium to be treated or the medium so treated until it is desired to be reused. Alternatively, yet another preferred aspect and benefit of this invention involves treating all or part of the liquid catalyst containing recycle medium of a such a continuous hydroformylation process with the reactivation procedure of this invention and returning the thus treated catalyst containing recycle medium to the reaction medium in the reactor of the continuous hydroformylation process. Such may be accomplished by any suitable method, e.g., drawing off a part of the recycle medium to an appropriate container, treating same and returning the treated medium, without any need for stopping or shutting down the continuous hydroformylation. Of course a portion of the hydroformylation reaction medium itself may be withdrawn from the reactor, and also so treated and returned to the reactor in the same fashion, if desired, without stopping or shutting down the continuous hydroformylation, as noted above.

Further, in addition to being readily returnable to or used as the reaction medium of the same hydroformylation process from whence the partially deactivated rhodium-tertiary organophosphine complex catalyst starting materials of Step (1) may be derived, the reactivated rhodium-tertiary organophosphine complex product of this invention, if desired, may be useful as the catalytic starting material or as a catalytic booster for any different conventional hydroformylation process.

Yet still another added benefit of this invention is that the use of an aqueous solution of tertiary alkanolamine in Step (2) of the process of this invention can be employed to simultaneously also improve or recapture catalytic activity loss in the starting hydroformylation catalyst that may be attributable to extrinsic halide and/or carboxylic acid poisoning, such as described in assignee's copending U.S. patent application Ser. No. 670,874 filed Mar. 18, 1991, now U.S. Pat. No. 5,183,943 (the entire disclosure of which is incorporated herein by reference thereto), in addition to helping improve or recapture that catalytic activity loss in the starting hydroformylation catalyst of this invention that is attributable to intrinsic deactivation (i.e. rhodium clusters as explained herein).

Such carboxylic acid, e.g., acetic acid, as employed herein, may also be employable in a similar manner along with other organic reagents, such as, e.g., acetylenic compounds containing halogen, carboxylate, sulfonate or phosphonium groups as disclosed in U.S. Pat. No. 4,861,918, as well as with other types of acetylenes such as acetyleneic ethers, e.g., methyl propargyl ether, aromatic acetylenic compounds, e.g., phenyl acetylene, acetylenic hydrocarbons, e.g., 1-hexyne and hydroxy substituted acetylenic hydrocarbons, e.g., 3-butyne-2-ol, instead of propargyl alcohol, to reactivate rhodium-tertiary organophosphine complex hydroformylation catalysts that have become at least partially deactivated due to intrinsic deactivation.

The following examples are illustrative of the present invention and are not to be regarded as limitative. It is to be understood that all parts, percentages and proportions referred to herein and in the appended claims are by weight unless otherwise indicated.

EXAMPLES 1 to 4

These examples illustrate improving the hydroformylation catalytic activity of a partially deactivated rhodium-triphenylphosphine complex hydroformylation catalyst composition that had been employed in a non-aqueous hydroformylation process directed to producing butyraldehyde by hydroformylating propylene and whose catalytic activity had declined from 100% active to about 36 percent of fresh catalyst.

Each experiment was conducted in essentially the same manner, the treatments being carried out in standard laboratory glassware and under an inert nitrogen atmosphere.

The procedure consisted essentially of removing all of the aldehyde product of said partially deactivated rhodium-triphenylphosphine complex catalyst composition and diluting it to a composition of about 9 weight percent triphenylphosphine (TPP) ligand and about 300 ppm rhodium, calculated as rhodium metal, with degassed Texanol ® solvent, a mixture of butyraldehyde trimers. Various amounts of propargyl alcohol and carboxylic acid, as reported in Table 1 below, were then added to 25 gram samples of said prepared rhodium-triphenylphosphine complex catalyst composition. Each solution was heated overnight at about 130° C. under a nitrogen atmosphere.

Each solution was then added to a single pass reactor and employed in a continuous single pass hydroformylation process directed to hydroformylating propylene (at about 100° C. using a gaseous mixture of about 100 psig. hydrogen, about 18 psig. carbon monoxide and about 23 psig. propylene) for from about 16 to about 28 hours, and their maximum catalytic activity determined. The results of each experiment as compared to the activity of fresh catalyst and the initial partially deactivated catalyst are given in the following Table 1.

TABLE 1

| Ex. No. | Propargyl Alcohol Molar Equivalents | Acetic Acid Molar Equivalents | Catalytic Activity[a] |
|---|---|---|---|
| 1 | None(Control) | None(Control) | 36% |
| 2 | 100(0.4 grams) | 25(0.11 grams) | 57%[b] |
| 3 | 100(0.4 grams) | 50(0.22 grams) | 67% |
| 4 | 100(0.4 grams) | 100(0.44 grams) | 74%[c] |

[a]Percent of Fresh Catalyst.
[b]Another experiment under similar conditions gave a catalyst activity of about 55%
[c]Another experiment under similar conditions gave a catalyst activity of about 80%

EXAMPLE 5

An organic liquid medium starting material was derived from a commercial continuous gaseous hydroformylation reaction involving the use of two reactors and the hydroformylation of propylene to butyraldehyde by reacting propylene, carbon monoxide and hydrogen in the presence of a hydroformylation reaction medium in said reactors, by shutting off the reactant feed gases, stopping the hydroformylation reaction and stripping essentially all (more than 99.5 percent) of the reactant gases from the reaction vessels and cycle lines of the system. The hydroformylation reaction mediums contained an average of about 75 percent by weight of butyraldehyde products, about 14 percent by weight of higher boiling aldehyde condensation by-products and other higher boilers, about 11 percent by weight of free triphenylphosphine ligand, and a solubilized rhodium complex hydroformylation catalyst consisting essentially of rhodium complexed with carbon monoxide and triphenylphosphine in an amount sufficient to provide about 340 ppm rhodium. The average catalytic activity of such hydroformylation reaction mediums had deactivated to about 40 percent of fresh catalyst. About half of said decline in activity was considered to be attributable to an inadvertent build-up of chloride poisoning and carboxylic acid inhibitors (i.e., extrinsic-type deactivation). The other half of said decline in activity was considered to be attributable to intrinsic deactivation (i.e., the formation of inactive rhodium complex clusters).

The hydroformylation reaction mediums in said reactors containing the deactivated rhodium-triphenylphosphine complex catalysts having a catalytic activity of only about 40 percent of fresh rhodium catalyst, as discussed above, were stripped down to remove about 25 percent by weight of aldehyde and lighter boiling components, e.g., propylene, propane, etc. During this period the two reactors were cooled to about 90° C. About 25 molar equivalents each of acetic acid and propargyl alcohol per mole of rhodium in each reactor were added to each reactor. The acetic acid was added first to minimize oligomerization of the propargyl alcohol. The reactors were then agitated and held at 90° C.

for 18 hours following said addition of acetic acid and propargyl alcohol. Extending the treatment time beyond 18 hours would, it is considered, have only undesirably increased aldehyde heavies buildup. Since the acetic acid and propargyl alcohol are miscible with the catalyst solution, circulation was maintained through the external heat exchange loop for the reactor system. At the end of said treatment, the reactor temperature was lowered to 60° C. and said circulation stopped to avoid emulsion formation during the aqueous tertiary alkanolamine wash. A mixture of a 12 percent aqueous triethanolamine solution in an amount equal to about 47 percent by weight (about 38 percent by volume) of the total weight of said treated hydroformylation catalyst containing reaction mediums was prepared in a separate catalyst mix tank and heated to about 60° C. The aqueous triethanolamine was then proportionately (one half to each reactor) transferred (pressurized) to the two reactors over a period of about 4 hours and after the aqueous solution had been transferred, each reactor was agitated for one hour. The mixed solution in each reactor was allowed to settle (separate) into two distinct aqueous and organic phases over a period of 4 hours. The aqueous phases were then drained from the hydroformylation reaction process system via outlet valves in discharge lines below the reactors. After said triethanolamine treatment and removal of the aqueous phase, the first reactor was heated back up to about 90° C. to prepare for a water wash, while the temperature of the second reactor was maintained at about 70° C. Clean water (i.e., steam condensate) in an amount equal to about 38 percent by weight of the weight of the rhodium-triphenylphosphine complex catalyst containing organic liquid phase composition remaining in each reactor after said triethanol amine treatment was transferred (pressurized) to each reactor over about a 4 hour transfer time. Each reactor was then agitated for one hour and the mixed solutions allowed to settle into two distinct aqueous and organic phases over 4 hours. The aqueous phases in both reactors were then drained from the hydroformylation reaction process system in the same manner as described above.

After the removal of said aqueous phases, the reactors were then heated to about 90° C. and the propylene hydroformylation restarted by feeding the propylene and syn gas reactants to said reactors in the normal fashion for commercial production of butyraldehyde. The activity of the rhodium-triphenylphosphine complex catalyst of said treated hydroformylation reaction mediums was found to have improved to about 60% of fresh rhodium catalyst within a day or two after restartup of the hydroformylation process, said improvement increasing to about 75% of fresh rhodium catalyst within about 7-10 days after said startup. Analytical results indicated that about half of the catalytic activity restoration was due to cleaving the rhodium clusters to produce active monomeric rhodium values, while the other half was due to the removal of said extrinisic chloride poisoning and carboxylic acid inhibitors. Of course, essentially all of the carboxylic acid employed along with the propargyl alcohol treatment was also removed via said triethanolamine wash. For instance, the chloride content in the hydroformylation reaction mediums was found to have been reduced from about 12 ppm to essentially undectable levels (less than 5 ppm).

Various modifications and variations of this invention will be obvious to a worker skilled in the art and it is to be understood that such modifications and variations are to be included within the purview of this application and the spirit and scope of the appended claims.

What is claimed is:

1. A process for improving the catalytic activity of a partially deactivated solubilized rhodium-tertiary organophosphine complex hydroformylation catalyst, which comprises (1) mixing under non-hydroformylating conditions, a organic liquid medium containing said solubilized partially deactivated complex catalyst, with propargyl alcohol and a carboxylic acid of the formula RCOOH wherein R represents hydrogen or an alkyl or aryl radical to obtain a treated solubilized rhodium-tertiary organophosphine complex product solution; and (2) removing from said product solution, the carboxylic acid employed in Step (1) to obtain a rhodium-tertiary organophosphine complex hydroformylation catalyst that is more catalytically active than said partially deactivated rhodium-tertiary organophosphine complex hydroformylation catalyst starting material of Step (1).

2. A process as defined in claim 1 wherein the carboxylic acid is acetic acid.

3. A process as defined in claim 2, wherein Step (2) comprises contacting said treated solubilized rhodium-tertiary organophosphine complex product of Step (1) with an aqueous solution of a tertiary alkanol amine and separating the organic phase from the aqueous phase of said aqueous tertiary alkanol amine treatment.

4. A process as defined in claim 3, wherein the tertiary organophosphine is triphenylphosphine or the sodium salt of 3-(diphenylphosphino) benzene sulfonic acid.

5. A process as defined in claim 2, wherein Step (2) comprises employing said treated solubilized rhodium-tertiary organophosphine complex product of Step (1) in a continuous non-aqueous hydroformylation process.

6. A process as defined in claim 3, wherein Step (2) consists essentially of
(a) mixing under non-hydroformylation conditions, the treated rhodium-tertiary organophosphine complex product solution of Step (1), with an aqueous solution containing from about 1 to about 25 percent by weight of a tertiary alkanolamine having the formula

wherein R represents a hydroxyalkyl radical having from 2 to 4 carbon atoms; wherein $R^1$ and $R^2$ each individually represent a radical selected from the group consisting of alkyl radicals having from 1 to 4 carbon atoms, hydroxyalkyl radicals having from 2 to 4 carbon atoms, and a phenyl radical, to form a water-soluble salt between said tertiary alkanolamine and the carboxylic acid employed in said Step (1);
(b) allowing the resulting mixture to settle into two distinct liquid phases;
(c) separating the aqueous phase which contains said salt from the organic phase containing the solubilized rhodium-tertiary organophosphine complex hydroformylation catalyst, and;
(d) washing the separated organic phase obtained by step (c) with water, to obtain an organic solubilized rhodium-tertiary organophosphine complex hydroformylation catalyst that is more catalytically active than said partially deactivated rhodium-tertiary organophosphine complex hydroformylation catalyst starting material of Step (1).

7. A process as defined in claim 6, wherein $R^1$ and $R^2$ each represent a hydroxyalkyl radical having from 2 to 4 carbon atoms.

8. A process as defined in claim 6, wherein the tertiary alkanolamine is triethanolamine.

9. A process as defined in claim 8, wherein the organic liquid medium starting material of Step (1) comprises all or part of the hydroformylation reaction medium of a continuous non-aqueous hydroformylation process.

10. A process as defined in claim 9, wherein Steps (1) and (2) are carried out in a hydroformylation reactor of said hydroformylation process.

11. A process as defined in claim 3, wherein the organic liquid medium starting material of Step (1) comprises all or a part of the liquid catalyst containing recycle medium of a continuous non-aqueous hydroformylation process.

12. A process as defined in claim 9, wherein said organic liquid medium starting material of Step (1) contains a rhodium-triphenylphosphine complex catalyst and at least 30 percent by weight of aldehyde.

13. A process as defined in claim 12, wherein the aldehyde is a mixture of n-butyraldehyde and isobutyraldehyde.

14. A process as defined in claim 9, wherein Step (d) consists of a single water wash.

15. A process as defined in claim 3, wherein said organic liquid medium of Step (1) contains at least 30 percent by weight of aldehyde.

* * * * *